US006344474B1

(12) United States Patent
Maruani et al.

(10) Patent No.: US 6,344,474 B1
(45) Date of Patent: Feb. 5, 2002

(54) USE OF CENTRAL CANNABINOID RECEPTOR ANTAGONISTS FOR REGULATING APPETENCE

(75) Inventors: Jeanne Maruani, Vailhauques; Philippe Soubrie, Saint Mathieu de Treviers, both of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/341,764

(22) PCT Filed: Jan. 28, 1998

(86) PCT No.: PCT/FR98/00154

§ 371 Date: Aug. 19, 1999

§ 102(e) Date: Aug. 19, 1999

(87) PCT Pub. No.: WO98/32441

PCT Pub. Date: Jul. 30, 1998

(30) Foreign Application Priority Data

Jan. 28, 1997 (FR) .............................. 97 00870

(51) Int. Cl.[7] .................... A61K 31/415; A61K 31/535; A61K 31/445
(52) U.S. Cl. .................... 514/406; 514/231.5; 514/329; 514/406
(58) Field of Search .............................. 514/406, 329, 514/231.5

(56) References Cited

U.S. PATENT DOCUMENTS 4,707,497 A 11/1987 Cecchi et al. ............... 514/647

FOREIGN PATENT DOCUMENTS

EP 0 656 354 6/1995

OTHER PUBLICATIONS

D. Shire et al., "Structural Features of the Central Cannabinoid CB1 Receptor Involved in the Binding of the Specific CB1 Antagonist SR 141716A", *J. Biol. Chem.*, 271 (12), 1996, pp. 6941–6946.

R. Pertwee et al., "AM640, A Competitive Cannabinoid Receptor Antagonist", *Life Sci.*, 56 (23/24), 1995, pp. 1941–1947.

M. Rinaldi–Carmona et al., "Biochemical and Pharmacological Characterisation of SR141716A, The First Potent and Selective Brain Cannabinoid Receptor Antagonist", *Life Sci.*, 56 (23/24), 1995, pp. 1949–1955.

F. Barth et al., "Cannabinoids: Receptors, Endogenous Ligands and A Newly Synthesized Antagonist", *NIDA Res. Monograph*, 162, 1996, pp. 52–53.

M. Rinaldi–Carmona et al., "Characterization and Distribution of Binding Sites for [$^3$H]–SR 141716A, A Selective Brain (CB1) Cannabinoid Receptor Antagonist, in Rodent Brain", *Life Sci.*, 58(15), 1996, pp. 1239–1247.

M. Rinaldi–Carmona et al., "SR141716A, A Potent and Selective Antagonist of the Brain Cannabinoid Receptor", *FEBS Letters*, 350 (2–3), 1994, pp. 240–244.

*Primary Examiner*—Theodore J. Criares
*Assistant Examiner*—Jennifer Kim
(74) *Attorney, Agent, or Firm*—Michael D. Alexander

(57) ABSTRACT

The invention relates to the use of a central cannabinoid receptor antagonist, by itself or in association with a compound for regulating metabolic disorders, especially a $\beta_3$-adrenergic receptor agonist, for the preparation of drugs useful in the treatment of appetency disorders.

13 Claims, No Drawings

USE OF CENTRAL CANNABINOID RECEPTOR ANTAGONISTS FOR REGULATING APPETENCE

The present invention relates to a novel use of antagonists of the central cannabinoid receptors or so-called $CB_1$ receptors.

More particularly, the invention relates to the use of $CB_1$ receptor antagonists for the preparation of drugs useful in the treatment of appetency disorders. The purpose of drugs useful in the treatment of appetency disorders is to regulate consumption desires, particularly desires to consume sugars, carbohydrates, alcohol or drugs and more generally to consume appetizing ingredients.

In the present description and in the claims, appetency disorders are understood as meaning:

disorders associated with a substance and especially abuse of a substance and/or dependency on a substance, disorders of food behaviors, especially those liable to cause excess weight, irrespective of its origin, for example: bulimia, appetency for sugars, non-insulin-dependent diabetes.

Substances are understood as meaning appetizing ingredients such as sugars, carbohydrates, alcohols or drugs.

The present invention therefore further relates to the use of a $CB_1$ receptor antagonist for the preparation of drugs useful in the treatment of bulimia and obesity, including obesity associated with type II diabetes (non-insulin-dependent diabetes), or more generally any disease resulting in the patient becoming overweight, and in the treatment of drug abuse or drug dependency.

Delta-9-tetrahydrocannabinol, or $\Delta^9$-THC, is the main active constituent extracted from Cannabis sativa (Tuner, 1985; in Marijuana, 84, Ed. Harvey, DY, IRL Press, Oxford).

The effects of cannabinoids are due to an interaction with high affinity specific receptors coupled to G proteins. Two types of receptors are currently described: the $CB_1$ receptors, which are present predominantly in the central nervous system (Devane et al., Molecular Pharmacology, 1988, 34, 605–613), and the $CB_2$ receptors, which are present in the immune system (Nye et al., The Journal of Pharmacology and Experimental Therapeutics, 1985, 234, 784–791; Kaminski et al., 1992, Molecular Pharmacology, 42, 736–742; Munro et al., Nature, 1993, 365, 61–65). Characterization of these receptors has been made possible by the development of synthetic ligands such as CP 55,940 (J. Pharmacol. Exp. Ther., 1988, 247, 1046–1051) and WIN 55212-2 (J. Pharmacol. Exp. Ther., 1993, 264, 1352–1363) and, more recently, by the discovery of the selective $CB_1$ receptor antagonist SR 141716 A (M. Rinaldi-Carmona et al., FEBS Lett., 1994, 350, 240–244).

Families of compounds having an affinity for the cannabinoid receptors have been described in several patents or patent applications, especially European patent application EP-576 357, which describes pyrazole derivatives, and patent application WO 96/02248, which describes especially benzofuran derivatives.

More particularly, N-piperidino-5-(4-chlorophenyl)-1-(2, 4-dichlorophenyl)-4-methylpyrazole-3-carboxamide, also called SR 141716, of the formula

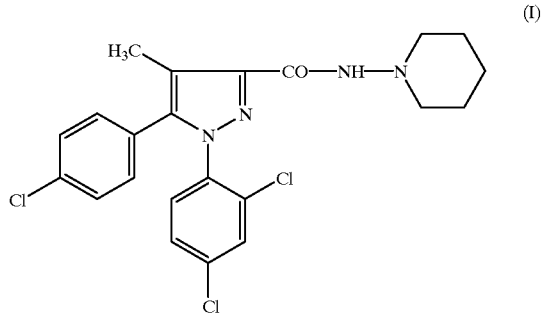

its pharmaceutically acceptable salts and their solvates are described in European patent application EP-656 354 as $CB_1$ central receptor antagonists.

SR 141716 A is the hydrochloride of SR 141716.

It is known that delta-9-tetrahydrocannabinol, whose international non-proprietary name is Dronabinol, is used in the treatment of anorexia, especially in patients suffering from AIDS (J. Pain Symptom Manage., 1995, 10 (2), 89–97) or cancer (J. Palliat. Care, 1994, 10 (1), 14–18).

It is further described that SR 141716 and its salts, which are central cannabinoid receptor antagonists, can be used in the treatment of appetite disorders, especially as anorexigenic agents, and in the treatment of disorders associated with the use of psychotropic substances.

Conventional anorexigenic agents cause an appetite reduction which is generally independent of the foods to be consumed.

Surprisingly, it has now been found that $CB_1$ receptor antagonists have a specific property by acting electively on consumption behavior disorders pertaining to appetizing substances.

Thus the administration of a $CB_1$ receptor antagonist makes it possible to regulate the desire to consume non-essential food items such as excess sugars, excess carbohydrates, alcohol or drugs.

In fact, after having conducted tests in animals, a novel behavior of the animal has been noted: animal tests have revealed a novel behavior: the animal no longer shows spontaneous appetency for the ingredient, for example sugar or alcohol, which usually brings pleasure to it. This lack of appetency also manifests itself when the animal has been pretreated with a neuropeptide known to increase the appetite, for example neuropeptide Y (NPY).

According to one of its aspects, the present invention relates to the use of a $CB_1$ receptor antagonist for the preparation of drugs useful in the treatment of appetency disorders.

The $CB_1$ receptor antagonists appropriate for the purposes of the invention are particularly the compounds of the formula

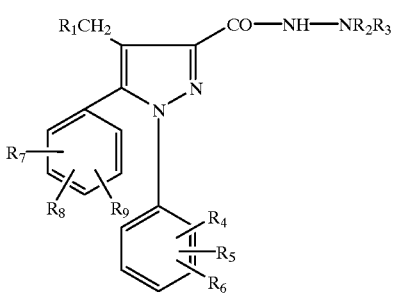

(II)

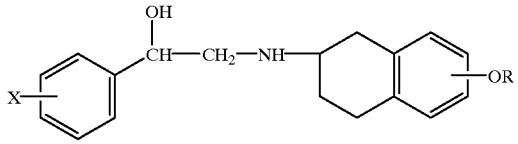

(III)

in which:

R₁ is hydrogen, a fluorine, a hydroxyl, a $(C_1-C_5)$alkoxy, a $(C_1-C_5)$alkylthio, a hydroxy$(C_1-C_5)$alkoxy, a group $-NR_{10}R_{11}$, a cyano, a $(C_1-C_5)$alkylsulfonyl or a $(C_1-C_5)$alkylsulfinyl;

R₂ and R₃ are a $(C_1-C_4)$alkyl or, together with the nitrogen atom to which they are bonded, form a saturated or unsaturated 5- to 10-membered heterocyclic radical which is unsubstituted or monosubstituted or polysubstituted by a $(C_1-C_3)$alkyl or by a $(C_1-C_3)$alkoxy;

R₄, R₅, R₆, R₇, R₈ and R₉ are each independently hydrogen, a halogen or a trifluoromethyl, and if R₁ is a fluorine, R₄, R₅, R₆, R₇, R₈ and/or R₉ can also be a fluoromethyl, with the proviso that at least one of the substituents R₄ or R₇ is other than hydrogen; and R₁₀ and R₁₁ are each independently hydrogen or a $(C_1-C_5)$alkyl, or R₁₀ and R₁₁, together with the nitrogen atom to which they are bonded, form a heterocyclic radical selected from pyrrolidin-1-yl, piperidin-1-yl, morpholin-4-yl and piperazin-1-yl, which is unsubstituted or substituted by a $(C_1-C_4)$alkyl, and their salts and their solvates.

More particularly, the present invention relates to the use of N-piperidino-5-(4-chlorophenyl)-1-(2,4-dichlorophenyl)-4-methylpyrazole-3-carboxamide, its pharmaceutically acceptable salts and their solvates for the preparation of drugs useful in the treatment of appetency disorders.

According to the present invention, the CB₁ receptor antagonists can also be used in association with another active principle for the preparation of drugs useful in the treatment of appetency disorders, especially in the treatment of disorders of food behaviors; it is possible to use a pharmaceutical composition comprising a CB₁ receptor antagonist in association with a compound for regulating metabolic disorders, especially a β₃-adrenergic receptor agonist, hereafter called a β₃-agonist.

Thus the present invention further relates to pharmaceutical compositions containing a CB₁ receptor antagonist and a regulator of metabolic disorders, for example a hypolipemic, hypolydemic or lipolytic. More particularly, the present invention relates to pharmaceutical compositions containing a CB₁ receptor antagonist and a β₃-agonist.

β₃-agonists which can be used according to the present invention are the compounds of the formula in which:

X is hydrogen, a halogen, a trifluoromethyl or a $(C_1-C_4)$ alkyl;

R is hydrogen or a methyl which is unsubstituted or substituted by a carboxyl or an alkoxycarbonyl in which the alkoxy is $(C_1-C_6)$, and their pharmaceutically acceptable salts, indicated in EP 0 211 721 and EP 0 303 546 as intestinal spasmolytics.

Among the compounds of formula (III), the following compounds:

2-[(7-hydroxy-1,2,3,4-tetrahydronaphth-2-yl)amino]-1-phenylethanol;
2-[(7-hydroxy-1,2,3,4tetrahydronaphth-2-yl)amino]-1-(3-chlorophenyl)-ethanol;
2-[(7-ethoxycarbonylmethoxy-1,2,3,4-tetrahydronaphth-2-yl)amino]-1-(3-chlorophenyl)ethanol;
2-[(7-ethoxycarbonylmethoxy-1,2,3,4-tetrahydronaphth-2-yl)amino]-1-phenylethanol;
(1R,2'RS)-2-[(7-hydroxy-1,2,3,4-tetrahydronaphth-2-yl)amino]-1-phenyl-ethanol;
(1S,2'RS)-2-[(7-hydroxy-1,2,3,4-tetrahydronaphth-2-yl)amino]-1-phenyl-ethanol;
(+)-(1R)-2-[(7-hydroxy-1,2,3,4-tetrahydronaphth-2-yl)amino]-1-phenyl-ethanol;
(+)-(1S)-2-[(7-hydroxy-1,2,3,4-tetrahydronaphth-2-yl)amino]-1-phenyl-ethanol;
(−)-(1R)-2-[(7-hydroxy-1,2,3,4-tetrahydronaphth-2-yl)amino]-1-phenyl-ethanol;
(−)-(1S)-2-[(7-hydroxy-1,2,3,4-tetrahydronaphth-2-yl)amino]-1-phenyl-ethanol;
N-[(2S)-7-ethoxycarbonylmethoxy-1,2,3,4-tetrahydronaphth-2-yl]-(2R)-2-(3-chlorophenyl)-2-hydroxyethanamine; and
N-[(2R)-7-methoxycarbonylmethoxy-1,2,3,4-tetrahydronaphth-2-yl]-(2R)-2-(3-chlorophenyl)-2-hydroxyethanamine, and their pharmaceutically acceptable salts, are particularly advantageous.

N-[(2S)-7-Ethoxycarbonylmethoxy-1,2,3,4-tetrahydronaphth-2-yl]-(2R)-2-(3-chlorophenyl)-2-hydroxyethanamine (SR 58611) and its pharmaceutically acceptable salts are very particularly advantageous, especially its salt with hydrochloric acid, SR 58611 A.

Other β₃-agonists which can be used according to the present invention are the compounds of the formula

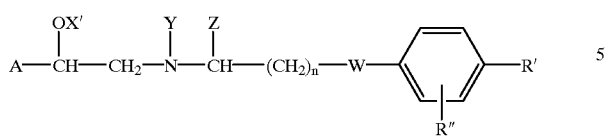

(IV)

in which:

n is 1,2 or 3;

A is a benzofuran-2-yl or a phenyl which is unsubstituted or substituted by one or two halogen atoms or by a $(C_1-C_4)$alkyl or a trifluoromethyl;

R' is:
  hydrogen;
  a $(C_1-C_6)$alkyl;
  a functional group selected from the following groups: hydroxyl; $(C_1-C_6)$-alkoxy; $(C_2-C_6)$alkenyloxy; $(C_2-C_6)$alkynyloxy; $(C_3-C_8)$cycloalkoxy; $(C_3-C_8)$-cycloalkyl$(C_1-C_6)$alkoxy; benzyloxy; phenoxy; mercapto; $(C_1-C_6)$alkylthio; $(C_2-C_6)$alkenylthio; $(C_2-C_6)$alkynylthio; $(C_3-C_8)$cycloalkylthio; $(C_3-C_8)$-cycloalkyl$(C_1-C_6)$alkylthio; benzylthio; phenylthio; $(C_1-C_6)$alkylsulfinyl; $(C_2-C_6)$alkenylsulfinyl; $(C_2-C_6)$alkynylsulfinyl; $(C_3-C_8)$ cycloalkylsulfinyl; $(C_3-C_8)$cycloalkyl$(C_1-C_6)$alkylsulfinyl; benzylsulfinyl; phenylsulfinyl; $(C_1-C_6)$alkylsulfonyl; $(C_2-C_6)$alkenylsulfonyl; $(C_2-C_6)$alkynylsulfonyl; $(C_3-C_8)$ cycloalkylsulfonyl; $(C_3-C_8)$cycloalkyl$(C_1-C_6)$ alkylsulfonyl; benzylsulfonyl; phenylsulfonyl; cyano; nitro; amino which is unsubstituted or substituted by one or two identical or different radicals selected from $(C_1-C_6)$alkyl, $(C_2-C_6)$alkenyl, $(C_2-C_6)$alkynyl, $(C_3-C_8)$cycloalkyl, $(C_3-C_8)$ cycloalkyl$(C_1-C_6)$alkyl, benzyl and phenyl groups; carboxyl; alkoxycarbonyl in which the alkoxy is $(C_1-C_6)$; $(C_2-C_6)$alkenyloxycarbonyl; $(C_2-C_6)$ alkynyloxycarbonyl; $(C_3-C_8)$cycloalkoxycarbonyl; $(C_3-C_8)$cycloalkyl$(C_1-C_6)$alkoxycarbonyl; benzyloxycarbonyl; phenoxycarbonyl; or carbamoyl which is unsubstituted or substituted on the amino group by one or two identical or different radicals selected from $(C_1-C_6)$alkyl, $(C_2-C_6)$alkenyl, $(C_2-C_6)$alkynyl, $(C_3-C_8)$-cycloalkyl, $(C_3-C_8)$ cycloalkyl$(C_1-C_6)$alkyl, benzyl and phenyl groups;
  a group R'" selected from the following groups: $(C_1-C_6)$alkyl substituted by a functional group; $(C_2-C_6)$alkenyl substituted by a functional group; $(C_2-C_6)$-alkynyl substituted by a functional group; phenyl$(C_1-C_6)$alkyl substituted on the phenyl by a $(C_1-C_6)$alkyl or by a functional group; phenyl $(C_2-C_6)$alkenyl substituted on the phenyl by a $(C_1-C_6)$alkyl or by a functional group; phenyl $(C_2-C_6)$alkynyl substituted on the phenyl by a $(C_1-C_6)$alkyl or by a functional group; benzyl substituted on the phenyl by a $(C_1-C_6)$alkyl or by a functional group; and phenyl which is unsubstituted or substituted by a $(C_1-C_6)$alkyl or by a functional group, the functional group being as defined above;
  a group O—R'", S—R'", SO—R'" or $SO_2$—R'", in which R'" is as defined above;
  a group NR'"R°, in which R'" is as defined above and R° is hydrogen or is as defined above for R'", or R'" and R°, together with the nitrogen to which they are bonded, form a group selected from pyrrolidino, piperidino and morpholino groups;
  a group COOR'" or a group CO—SR'", in which R'" is as defined above;
  a group CONR'"R°, in which R'" is as defined above and R° is hydrogen or is as defined above for R'", or R'" and R°, together with the nitrogen to which they are bonded, form a group selected from pyrrolidino, piperidino and morpholino groups;
  a group $SO_2$NR'"R°, in which R'" is as defined above and R° is hydrogen or is as defined above for R'", or R'" and R°, together with the nitrogen to which they are bonded, form a group selected from pyrrolidino, piperidino and morpholino groups;

R"is hydrogen; a halogen; a $(C_1-C_6)$alkyl; a functional group as defined above; a group OR'", R'" being as defined above; a group COOR'", R'" being as defined above; or a group CONR'"R°, in which R'" is as defined above and R° is hydrogen or is as defined above for R'", or R'" and R°, together with the nitrogen to which they are bonded, form a group selected from pyrrolidino, piperidino and morpholino groups;

W is a direct bond or an oxygen atom;

X' is hydrogen, a $(C_1-C_6)$alkyl or a $(C_1-C_6)$ alkylcarbonyl;

Y is hydrogen or a group A'—CH(OH)—$CH_2$—, A' being identical to A but other than benzofuran-2-yl; or X' and Y, taken together, form a methylene group optionally substituted by an alkoxycarbonyl in which the alkoxy is $(C_1-C_6)$; an ethylene group optionally substituted by an oxo group; or a 1,3-propylene group;

Z is hydrogen or a $(C_1-C_6)$alkyl, and their pharmaceutically acceptable salts, indicated in EP 0 255 415 as intestinal spasmolytics.

Other $\beta_3$-agonists which can also be used according to the present invention are the compounds of the formula

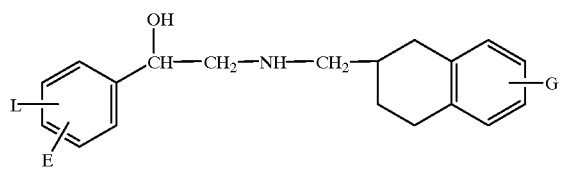

(V)

in which:

E is hydrogen, a $(C_1-C_4)$alkyl, a $(C_1-C_4)$alkoxy, a phenyl, a nitro, a halogen atom or a trifluoromethyl;

L is hydrogen, a $(C_1-C_4)$alkyl, a $(C_1-C_4)$alkoxy, a phenyl, a nitro or a halogen atom; or E and L together are a group —CH=CH—CH=CH— or —$CH_2$—$CH_2$—$CH_2$—$CH_2$—; and G is hydrogen, a chlorine atom, a hydroxyl or a group OG', in which G' is a $(C_1-C_4)$alkyl which is unsubstituted or substituted by a hydroxyl, $(C_1-C_4)$alkoxy, $(C_1-C_4)$alkoxycarbonyl, carboxyl or $(C_3-C_7)$ cycloalkyl; a $(C_3-C_7)$cycloalkyl; or a $(C_2-C_4)$alkanoyl, and their pharmaceutically acceptable salts, indicated in EP 0 436 435 as intestinal spasmolytics.

Among the compounds of formula (V), N-[(2R)-(6-hydroxy-1,2,3,4-tetrahydronaphth-2-yl)methyl]-(2R)-2-hydroxy-2-(3-chlorophenyl)ethanamine (SR 59104), N-[(2R)-(7-methoxy-1,2,3,4-tetrahydronaphth-2-yl) methyl]-(2R)-2-hydroxy-2-(3-chlorophenyl)ethanamine (SR59119) and their pharmaceutically acceptable salts are particularly advantageous compounds.

Other advantageous $\beta_3$-agonists according to the present invention are the compound BRL 35135 described in EP 23385; the compound CL 316243 described in U.S. Pat. No. 5,061,727; the compound AZ 002 described in EP 218440; the compound BMS 187257 described in U.S. Pat. No. 5,321,036; the compound ZD 7114 described in EP 473 285; the compound RO 40-2148 described in Am. J. Clin. Nutr., 1992, 55 (1, Suppl.), 249S –251S; and the products described in the following patents/patent applications: WO 96/35671, WO 96/35670, WO 96/16038, WO 96/04233, WO 95/33724, WO 95/29159, EP 659737, WO 95/04047, EP 516349, EP 473285, EP 23385, EP 21636, EP 7205, JP 08198866, JP 08165276, JP 08157470, WO 96/16938, EP 714883, WO 96/04234, U.S. Pat. Nos. 5,488,064, 5,482,971, 5,491,134, WO 95/29159, WO 95/33724, ZA 9409874, WO 95/29903, U.S. Pat. No. 5,461,163, WO 95/25104, EP 659737, JP 07112958, WO 95/8527, WO 95/07284, JP 07025756, WO 95/03289, WO 95/04047, WO 95/01170, WO 94/29290, U.S. Pat. No. 5,373,020, JP 06293664, WO 94/12166 and U.S. Pat. No. 5,451,677.

For its use as a drug, a $CB_1$ receptor antagonist compound, by itself or in association with a $\beta_3$-agonist, must be formulated as a pharmaceutical composition.

In the pharmaceutical compositions of the present invention for oral, sublingual, subcutaneous, intramuscular, intravenous, transdermal, local or rectal administration, the active principle, by itself or in association with another active principle, can be administered to animals and humans in unit forms of administration mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

In the pharmaceutical compositions of the present invention, the active principle or active principles are generally formulated in dosage units. The dosage unit contains from 0.5 to 1000 mg, advantageously from 1 to 500 mg and preferably from 2 to 200 mg of $CB_1$ receptor antagonist per dosage unit for daily administration.

In cases where 2 active principles are associated, the dosage unit contains from 0.5 to 600 mg, advantageously from 1 to 400 mg and preferably from 2 to 200 mg of $CB_1$ receptor antagonist compound and from 0.5 to 600 mg, advantageously from 2 to 400 mg and preferably from 10 to 250 mg of the other active principle, especially a $\beta_3$-agonist.

When a solid composition is prepared in the form of tablets, a wetting agent such as sodium laurylsulfate can be added to the micronized or non-micronized active principle (s) and the whole is mixed with a pharmaceutical vehicle such as silica, starch, lactose, magnesium stearate, talcum or the like. The tablets can be coated with sucrose, a variety of polymers or other appropriate substances, or else they can be treated so as to have a sustained or delayed activity and so as to release a predetermined amount of active principle continuously.

A preparation in the form of gelatin capsules is obtained by mixing the active principle or active principles with a diluent, such as a glycol or a glycerol ester, and incorporating the resulting mixture into soft or hard gelatin capsules.

A preparation in the form of a syrup or elixir can contain the active principle or active principles together with a sweetener, which is preferably calorie-free, methylparaben and propylparaben as antiseptics, a flavoring and an appropriate color.

The water-dispersible powders or granules can contain the active principle or active principles mixed with dispersants or wetting agents or with suspending agents such as polyvinylpyrrolidone or polyvidone, as well as with sweeteners or taste correctors.

Rectal administration is effected using suppositories, which are prepared with binders melting at the rectal temperature, for example cocoa butter or polyethylene glycols.

Parenteral administration is effected using aqueous suspensions, isotonic saline solutions or injectable sterile solutions containing pharmacologically compatible dispersants and/or solubilizing agents, for example propylene glycol or butylene glycol.

Thus, to prepare an aqueous solution for intravenous injection, it is possible to use a cosolvent, for example an alcohol such as ethanol or a glycol such as polyethylene glycol or propylene glycol, and a hydrophilic surfactant such as Tween® 80. To prepare an oily solution for intramuscular injection, the active principle can be solubilized with a triglyceride or a glycerol ester.

Transdermal administration can be effected using patches in multilaminar form or with a reservoir in which the active principle is in alcoholic solution.

The active principle or active principles can also be formulated as microcapsules or microspheres, optionally with one or more carriers or additives.

The active principle or active principles can also be presented in the form of complexes with a cyclodextrin, for example $\alpha$-, $\beta$- or $\gamma$-cyclodextrin, 2-hydroxy-propyl-$\beta$-cyclodextrin or methyl-$\beta$-cyclodextrin.

Among the sustained release forms useful in the case of chronic treatments, it is possible to use implants. These can be prepared in the form of an oily suspension or in the form of a suspension of microspheres in an isotonic medium.

According to another aspect of the invention, the $CB_1$ receptor antagonist and the regulator of metabolic disorders, especially the $\beta_3$-agonist, can be administered simultaneously, sequentially or over a period of time in the treatment of appetency disorders, especially in the treatment of disorders of food behaviors.

The invention therefore further relates to a kit for the treatment of appetency disorders by the administration, simultaneously, sequentially or over a period of time, of a $CB_1$ receptor antagonist and a regulator of metabolic disorders, especially a $\beta_3$-agonist, in which kit said $CB_1$ receptor antagonist and said regulator of metabolic disorders, especially said $\beta_3$-agonist, are in separate compartments and optionally in different packagings.

More particularly, said kit contains N-piperidino-5-(4-chlorophenyl)-1-(2,4-dichlorophenyl)-4-methylpyrazole-3-carboxamide, one of its pharmaceutically acceptable salts or one of their solvates, and N-[(2S)-7-ethoxycarbonylmethoxy-1,2,3,4-tetrahydronaphth-2-yl]-(2R)-2-(3-chlorophenyl)-2-hydroxyethanamine or one of its pharmaceutically acceptable salts.

According to another of its aspects, the invention further relates to a method of treating appetency disorders, especially a method of treating disorders of food behaviors, which consists in administering, to a subject in need thereof, a (therapeutically) effective amount of a $CB_1$ receptor antagonist as defined above. Said $CB_1$ receptor antagonist can advantageously be used in association with a regulator of metabolic disorders, especially a $\beta_3$ agonist, as defined above. In particular, the $CB_1$ receptor antagonist and the regulator of metabolic disorders can be administered simultaneously, sequentially or over a period of time.

TEST No. 1: Effect of SR 141716 A on the intake of a sucrose solution in rats

The experiment is performed according to W. C. Lynch et al., Physiol. Behav., 1993, 54, 877–880.

Male Sprague-Dawley rats weighing 190 to 210 g are under a normal light cycle (from 7 am to 7 pm) and receive water and food ad libitum.

For 6 days, between 11 am and 3 pm, the food and the water bottles are withdrawn and the rats are given a 5% sucrose solution to drink.

Rats drinking less than 3 g of sucrose solution are eliminated.

On the seventh day the test is carried out according to the following procedure:

9 am: withdrawal of food, 10 am: oral administration of SR 141716 A, 11 am=T0: introduction of bottles containing a weighed sucrose solution , T0+1 hour, T0+2 hours, T0+3 hours, T0+4 hours: measurement of the sucrose consumption by weighing of the bottles.

TABLE 1

| Treatment po | Number of rats | Consumption of sucrose solution in g | | | |
|---|---|---|---|---|---|
| | | 1 hour | 2 hours | 3 hours | 4 hours |
| Vehicle 2 ml/kg | 8 | 11.33 ± 2.50 | 17.74 ± 4.00 | 22.50 ± 4.83 | 28.34 ± 5.01 |
| SR 141716 A 0.3 mg/kg | 6 | 5.18 ± 1.61 | 9.18 ± 2.12 | 12.49 ± 4.47 | 16.10 ± 3.95 |
| SR 141716 A 1 mg/kg | 6 | 3.27* ± 1.40 | 3.61** ± 1.40 | 5.65* ± 2.23 | 7.43** ± 2.81 |
| SR 141716 A 3 mg/kg | 6 | 2.95* ± 1.20 | 5.41* ± 1.33 | 6.96* ± 2.15 | 8.58** ± 2.92 |

*$p < 0.05$;
**$p < 0.01$, Dunnett test

It is seen from the results reported in TABLE 1 that the administration of SR 141716 A very considerably reduces the consumption of aqueous sugar solution at or above a dose of 0.3 mg/kg.

TEST No. 2: Effect of SR 141716 A on the consumption of an alcohol solution in mice Male C 57 BL 6 mice (Iffa-Credo) are isolated on the day of their arrival in an animal housing under a reverse cycle (night from 10 am to 10 pm) with 2 bottles filled with water. After 1 week, one of the bottles of water is replaced with a bottle filled with a 10% alcohol solution for 6 hours of the test. Each day, 30 minutes before the bottle of alcohol is introduced, the mice are treated subcutaneously with SR 141716 A. The amounts of alcohol and water consumed are measured after 6 hours. The test is repeated for 4 days.

TABLE 2

| Treatment mg/kg/sc SR 141716 A | Number of mice | Amount of alcohol consumed in g on D4 | Amount of water consumed in g |
|---|---|---|---|
| Vehicle | 20 | 1.9 ± 0.1 | 1.1 ± 0.1 |
| 0.1 | 10 | 1.4 ± 0.2 | 1.1 ± 0.3 |
| 0.3 | 10 | 1.3 ± 0.2 | 1.1 ± 0.3 |
| 1 | 10 | 1.1 ± 0.2** | 1.3 ± 0.1 |
| 3 | 10 | 1.0 ± 0.2** | 1.6 ± 0.3 |

**$p < 0.01$, Dunnett test

The results show that the alcohol consumption decreases very substantially for the treated animals: from 1.9±0.1 g for an untreated animal to 1.0±0.2 g for an animal receiving 3 mg/kg of SR 141716 A; the water consumption increased in parallel: from 1.1±0.1 to 1.6±0.3 g.

EXAMPLE 1

Gelatin Capsule Containing a 1 mg Dose of $CB_1$ Receptor Antagonist

| | |
|---|---|
| Micronized SR 141716 | 1.00 mg |
| Corn starch | 51.00 mg |
| Lactose monohydrate | 103.33 mg |
| Polyvidone | 4.30 mg |
| Sodium laurylsulfate | 0.17 mg |
| Crosslinked sodium carboxymethyl cellulose | 8.50 mg |
| Purified water: QS for wet granulation | |
| Magnesium stearate | 1.70 mg |

For a no. 3 opaque white gelatin capsule filled to 170 mg

EXAMPLE 2

Gelatin Capsule Containing a 10 mg Dose of $CB_1$ Receptor Antagonist

| | |
|---|---|
| Micronized SR 141716 A | 10.00 mg |
| Corn starch | 51.00 mg |
| Lactose monohydrate | 94.33 mg |
| Polyvidone | 4.30 mg |
| Sodium laurylsulfate | 0.17 mg |
| Crosslinked sodium carboxymethyl cellulose | 8.50 mg |
| Purified water: QS for wet granulation | |
| Magnesium stearate | 1.70 mg |

For a no. 3 opaque white gelatin capsule filled to 170 mg

EXAMPLE 3

Gelatin Capsule Containing a 30 mg Dose of $CB_1$ Receptor Antagonist

| | |
|---|---|
| Micronized SR 141716 | 30.00 mg |
| Corn starch | 51.00 mg |
| Lactose monohydrate | 74.33 mg |
| Polyvidone | 4.30 mg |
| Sodium laurylsulfate | 0.17 mg |
| Crosslinked sodium carboxymethyl cellulose | 8.50 mg |
| Purified water: QS for wet granulation | |
| Magnesium stearate | 1.70 mg |

For a no. 3 opaque white gelatin capsule filled to 170 mg

EXAMPLE 4

Tablet Containing a 30 mg Dose of $CB_1$ Receptor Antagonist

| | |
|---|---|
| Micronized SR 141716 | 30.00 mg |
| Lactose monohydrate | QS |
| Corn starch | 40.00 mg |
| Hydroxypropyl methyl cellulose 6 cP | 5.00 mg |
| Purified water: QS for wet granulation | |
| Crosslinked sodium carboxymethyl cellulose | 10.00 mg |
| Magnesium stearate | 2.00 mg |

For a finished tablet of 200 mg

EXAMPLE 5

Tablet Containing 30 mg of $CB_1$ Receptor Antagonist and 200 mg of $\beta_3$-agonist

| | |
|---|---|
| Micronized SR 141716 | 30.00 mg |
| SR 58611 A expressed as the base | 200.00 mg |
| Lactose monohydrate | QS |
| Polyvidone | 15.00 mg |
| Purified water: QS for wet granulation | |
| Crosslinked sodium carboxymethyl cellulose | 10.00 mg |
| Magnesium stearate | 5.00 mg |

For a finished tablet of 500 mg

EXAMPLE 6

Tablet Containing 10 mg of $CB_1$ Receptor Antagonist and 100 mg of $\beta_3$-agonist

| | |
|---|---|
| Micronized SR 141716 | 10.00 mg |
| SR 58611 A expressed as the base | 100.00 mg |
| Corn starch | 30 mg |
| Lactose monohydrate | QS |
| Hydroxypropyl methyl cellulose 6 cP | 5.00 mg |
| Purified water: QS for wet granulation | |
| Sodium carboxymethyl starch | 6.00 mg |
| Magnesium stearate | 3.00 mg |

For a finished tablet of 300 mg

What is claimed is:

1. A method for the treatment of appetency disorders which comprises administering to a subject in need thereof an effective amount of a $CB_1$ receptor antagonist.

2. A method according to claim 1 wherein the $CB_1$ receptor antagonist is a compound of the formula

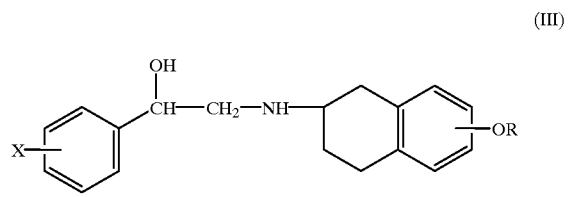

(II)

in which:

$R_1$ is hydrogen, a fluorine, a hydroxyl, a $(C_1-C_5)$alkoxy, a $(C_1-C_5)$alkylthio, a hydroxy$(C_1-C_5)$alkoxy, a group $-NR_{10}R_{11}$, a cyano, a $(C_1-C_5)$alkylsulfonyl or a $(C_1-C_5)$alkylsulfinyl;

$R_2$ and $R_3$ are a $(C_1-C_4)$alkyl or, together with the nitrogen atom to which they are bonded, form a saturated or unsaturated 5- to 10-membered heterocyclic radical which is unsubstituted or monosubstituted or polysubstituted by a $(C_1-C_3)$alkyl or by a $(C_1-C_3)$alkoxy;

$R_4$, $R_5$, $R_6$, $R_7$, $R_8$ and $R_9$ are each independently hydrogen, a halogen or a trifluoromethyl, and if $R_1$ is a fluorine, $R_4$, $R_5$, $R_6$, $R_7$, $R_8$ and/or $R_9$ can also be a fluoromethyl, with the proviso that at least one of the substituents $R_4$ or $R_7$ is other than hydrogen;

$R_{10}$ and $R_{11}$ are each independently hydrogen or a $(C_1-C_5)$alkyl, or $R_{10}$ and $R_{11}$, together with the nitrogen atom to which they are bonded, form a heterocyclic radical selected from pyrrolidin-1-yl, piperidin-1-yl, morpholin-4-yl and piperazin-1-yl, which is unsubstituted or substituted by a $(C_1-C_4)$alkyl, one of its salts or one of their solvates.

3. A method according to claim 2 wherein the $CB_1$ receptor antagonist is N-piperidino-5-(4-chlorophenyl)-1-(2,4-dichlorophenyl)-4-methylpyrazole-3-carboxamide, one of its pharmaceutically acceptable salts or one of their solvates.

4. A method according to claim 1 wherein the $CB_1$ receptor antagonist is associated with a regulator of metabolic disorders.

5. A method according to claim 4 wherein said regulator of metabolic disorders is a $\beta_3$-agonist.

6. A method according to claim 5 wherein said $\beta_3$-agonist is a compound of the formula

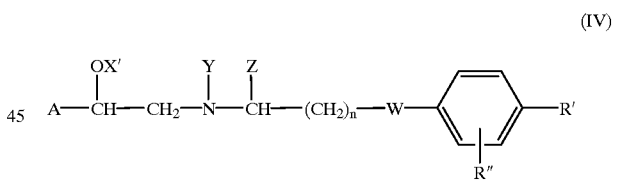

(III)

in which:

X is hydrogen, a halogen, a trifluoromethyl or a $(C_1-C_4)$alkyl; and

R is hydrogen or a methyl which is unsubstituted or substituted by a carboxyl or an alkoxycarbonyl in which the alkoxy is $(C_1-C_6)$, or one of its pharmaceutically acceptable salts.

7. A method according to claim 6 wherein said $\beta_3$-agonist is N-[(2S)-7-ethoxycarbonylmethoxy-1,2,3,4-tetrahydronaphth-2-yl]-(2R)-2-(3-chlorophenyl)-2-hydroxyethanamine or one of its pharmaceutically acceptable salts.

8. A method according to claim 5 wherein said $\beta_3$-agonist is a compound of the formula

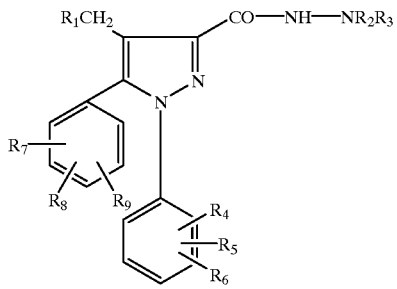

(IV)

in which:

n is 1, 2 or 3;

A is a benzofuran-2-yl or a phenyl which is unsubstituted or substituted by one or two halogen atoms or by a $(C_1-C_4)$alkyl or a trifluoromethyl;

R' is:

hydrogen;

a $(C_1-C_6)$alkyl;

a functional group selected from the following groups: hydroxyl; $(C_1-C_6)$alkoxy; $(C_2-C_6)$alkenyloxy; $(C_2-C_6)$alkynyloxy; $(C_3-C_8)$cycloalkoxy; $(C_3-C_8)$-cycloalkyl$(C_1-C_6)$alkoxy; benzyloxy; phenoxy; mercapto; $(C_1-C_6)$alkylthio; $(C_2-C_6)$alkenylthio; $(C_2-C_6)$alkynylthio; $(C_3-C_8)$cycloalkylthio; $(C_3-C_8)$cycloalkyl$(C_1-C_6)$alkylthio; benzylthio; phenylthio; $(C_1-C_6)$alkylsulfinyl; $(C_2-C_6)$alkenylsulfinyl; $(C_2-C_6)$alkynylsulfinyl; $(C_3-C_8)$cycloalkylsulfinyl; $(C_3-C_8)$cycloalkyl$(C_1-C_6)$ alkylsulfinyl; benzylsulfinyl; phenylsulfinyl; $(C_1-C_6)$alkylsulfonyl; $(C_2-C_6)$-alkenylsulfonyl; $(C_2-C_6)$alkynylsulfonyl; $(C_3-C_8)$cycloalkylsulfonyl; $(C_3-C_8)$-cycloalkyl$(C_1-C_6)$alkylsulfonyl; benzylsulfonyl; phenylsulfonyl; cyano; nitro; amino which is unsubstituted or substituted by one or two identical or different radicals selected from $(C_1-C_6)$alkyl, $(C_2-C_6)$alkenyl, $(C_2-C_6)$alkynyl, $(C_3-C_8)$ cycloalkyl, $(C_3-C_8)$ cycloalkyl$(C_1-C_6)$alkyl, benzyl and phenyl groups; carboxyl; alkoxycarbonyl in which the alkoxy is $(C_1-C_6)$; $(C_2-C_6)$alkenyloxycarbonyl; $(C_2-C_6)$ alkynyloxy-carbonyl; $(C_3-C_8)$cycloalkoxycarbonyl; $(C_3-C_8)$cycloalkyl$(C_1-C_6)$alkoxycarbonyl; benzyloxycarbonyl; phenoxycarbonyl; or carbamoyl which is unsubstituted or substituted on the amino group by one or two identical or different radicals selected from $(C_1-C_6)$alkyl, $(C_2-C_6)$alkenyl, $(C_2-C_6)$alkynyl, $(C_3-C_8)$cycloalkyl, $(C_3-C_8)$-cycloalkyl$(C_1-C_6)$alkyl, benzyl and phenyl groups;

a group R'" selected from the following groups: $(C_1-C_6)$alkyl substituted by a functional group; $(C_2-C_6)$alkenyl substituted by a functional group; $(C_2-C_6)$alkynyl substituted by a functional group; phenyl$(C_1-C_6)$alkyl substituted on the phenyl by a $(C_1-C_6)$alkyl or by a functional group; phenyl $(C_2-C_6)$alkenyl substituted on the phenyl by a $(C_1-C_6)$alkyl or by a functional group; phenyl $(C_2-C_6)$alkynyl substituted on the phenyl by a $(C_1-C_6)$alkyl or by a functional group; benzyl substituted on the phenyl by a $(C_1-C_6)$alkyl or by a functional group; and phenyl which is unsubstituted or substituted by a $(C_1-C_6)$alkyl or by a functional group, the functional group being as defined above;

a group O—R'", S—R'", SO—R'" or SO$_2$—R'", in which R'" is as defined above;

a group NR'"R°, in which R'" is as defined above and R° is hydrogen or is as defined above for R'", or R'" and R°, together with the nitrogen to which they are bonded, form a group selected from pyrrolidino, piperidino and morpholino groups;

a group COOR'" or a group CO—SR'", in which R'" is as defined above;

a group CONR'"R°, in which R'" is as defined above and R° is hydrogen or is as defined above for R'", or R'" and R°, together with the nitrogen to which they are bonded, form a group selected from pyrrolidino, piperidino and morpholino groups;

a group SO$_2$NR'"R°, in which R'" is as defined above and R° is hydrogen or is as defined above for R'", or R'" and R°, together with the nitrogen to which they are bonded, form a group selected from pyrrolidino, piperidino and morpholino groups;

R" is hydrogen; a halogen; a $(C_1-C_6)$alkyl; a functional group as defined above; a group OR'", R'" being as defined above; a group COOR'", R'" being as defined above; or a group CONR'"R°, in which R'" is as defined above and R° is hydrogen or is as defined above for R'", or R'" and R°, together with the nitrogen to which they are bonded, form a group selected from pyrrolidino, piperidino and morpholino groups;

W is a direct bond or an oxygen atom;

X' is hydrogen, a $(C_1-C_6)$alkyl or a $(C_1-C_6)$ alkylcarbonyl;

Y is hydrogen or a group A'—CH(OH)—CH$_2$—, A' being identical to A but other than benzofuran-2-yl; or X' and Y, taken together, form a methylene group optionally substituted by an alkoxycarbonyl in which the alkoxy is $(C_1-C_6)$; an ethylene group optionally substituted by an oxo group; or a 1,3-propylene group;

Z is hydrogen or a $(C_1-C_6)$alkyl, or one of its pharmaceutically acceptable salts.

9. A method according to claim 5 wherein said β$_3$-agonist is a compound of the formula

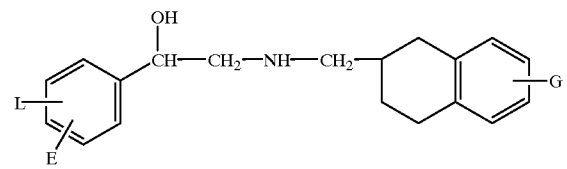

(V)

in which:

E is hydrogen, a $(C_1-C_4)$alkyl, a $(C_1-C_4)$alkoxy, a phenyl, a nitro, a halogen atom or a trifluoromethyl;

L is hydrogen, a $(C_1-C_4)$alkyl, a $(C_1-C_4)$alkoxy, a phenyl, a nitro or a halogen atom; or E and L together are a group —CH═CH—CH═CH— or —CH$_2$—CH$_2$—CH$_2$—CH$_2$—; and G is hydrogen, a chlorine atom, a hydroxyl or a group OG', in which G' is a $(C_1-C_4)$alkyl which is unsubstituted or substituted by a hydroxyl, $(C_1-C_4)$alkoxy, $(C_1-C_4)$alkoxycarbonyl, carboxyl or $(C_3-C_7)$ cycloalkyl; a $(C_3-C_7)$cycloalkyl; or a $(C_2-C_4)$alkanoyl, or one of its pharmaceutically acceptable salts.

10. A method according to claim 5 wherein the CB$_1$ receptor antagonist is N-piperidino-5-(4-chlorophenyl)-1-(2,4-dichlorophenyl)-4-methylpyrazole-3-carboxamide, one of its pharmaceutically acceptable salts or one of their solvates and the β$_3$-agonist is N-[(2S)-7-ethoxycarbonylmethoxy-1,2,3,4-tetrahydronaphth-2-yl]-(2R)-2-(3-chlorophenyl)-2-hydroxyethanamine or one of its pharmaceutically acceptable salts.

11. A method according to claim 1 for the treatment of appetency disorders selected from the group consisting of the regulation of consumption desires, disorders associated with a substance, food behaviors, obesity, obesity associated with non-insulin-dependent diabetes, any disease resulting in the patient becoming overweight, bulimia, drug abuse, drug dependency, the desire to consume non-essential food items and the spontaneous appetency for a food item which usually brings pleasure.

12. A method according to claim 11 wherein the non-essential food items are excess sugars, excess carbohydrates, alcohol or drugs and the food item which usually brings pleasure is alcohol or sugar.

13. A method according to claim 11 in which the CB$_1$ receptor antagonist is N-piperidino-5-(4-chlorophenyl)-1-(2,4-dichlorophenyl)-4-methylpyrazole-3-carboxamide, one of its pharmaceutically acceptable salts or one of their solvates.

* * * * *